United States Patent [19]

Habdas et al.

[11] 4,229,275
[45] Oct. 21, 1980

[54] SOLID ELECTROLYTE OXYGEN SENSOR AND METHOD OF MAKING SAME

[75] Inventors: Edward P. Habdas; Jon D. Aaron, both of Decatur, Ala.

[73] Assignee: UOP Inc., Des Plaines, Ill.

[21] Appl. No.: 55,573

[22] Filed: Jul. 9, 1979

[51] Int. Cl.² .................. G01N 27/58; C04B 37/00
[52] U.S. Cl. .................................. 204/195 S; 264/61
[58] Field of Search .............. 204/195 S, 1 S; 264/61; 29/592, 595

[56] References Cited

U.S. PATENT DOCUMENTS

| | | | |
|---|---|---|---|
| 4,119,513 | 10/1978 | Shum et al. | 204/195 S |
| 4,123,344 | 10/1978 | Davis | 204/195 S |

Primary Examiner—G. L. Kaplan
Attorney, Agent, or Firm—James R. Hoatson, Jr.; Barry L. Clark; William H. Page, II

[57] ABSTRACT

Oxygen sensor with a disc type solid electrolyte has the disc sealed in a shrinkable ceramic tube by the pressure which is developed and the surface glazing which takes place as the tube is fired. The tube is preferably formed of forsterite which can shrink about 25% during firing, thus causing the tube to become slightly bulged out in the region of the disc due to the interference fit produced by the shrinkage. The porous electrodes on the top and bottom surfaces of the disc are preferably omitted from a small region near one edge of the top and bottom surfaces but are continued as a stripe or band down the edge from a diametrically opposite portion of each surface, the stripes and unelectroded areas associated with the respective surfaces being spaced to prevent electrical shorting. The disc stripes are pressure bonded during firing of the tube to a pair of spaced lead stripes on the inside tube surface.

8 Claims, 8 Drawing Figures

U.S. Patent
Oct. 21, 1980
4,229,275
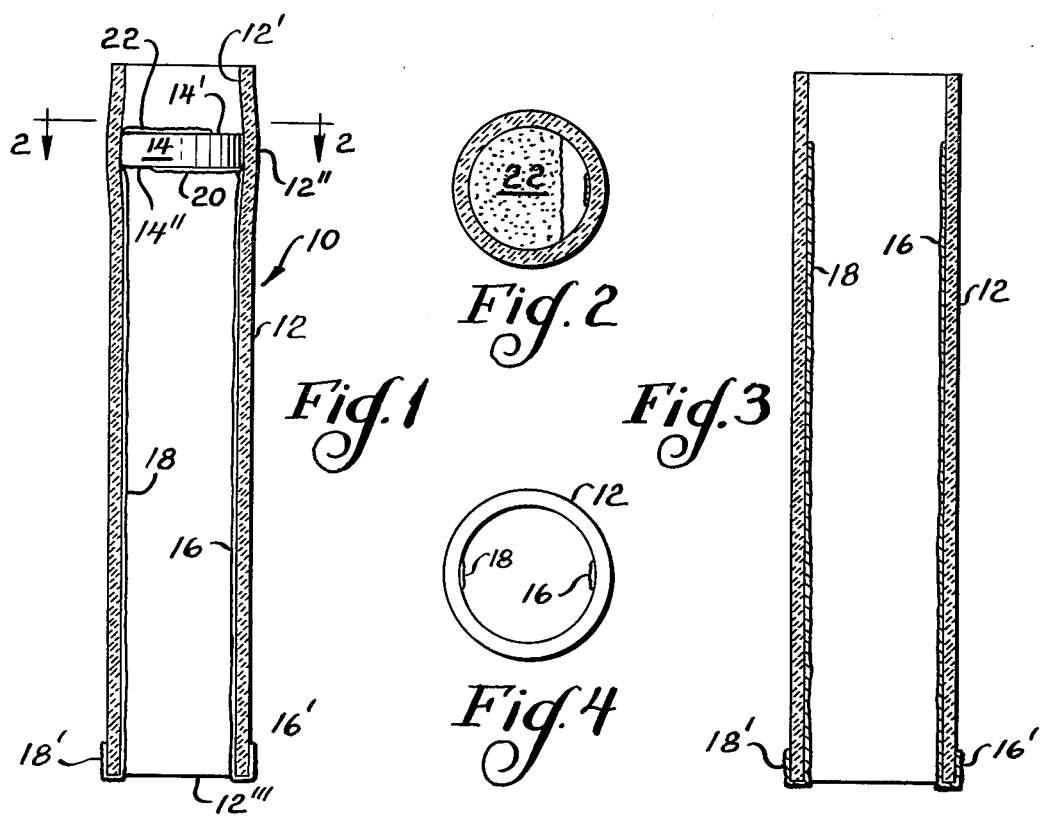
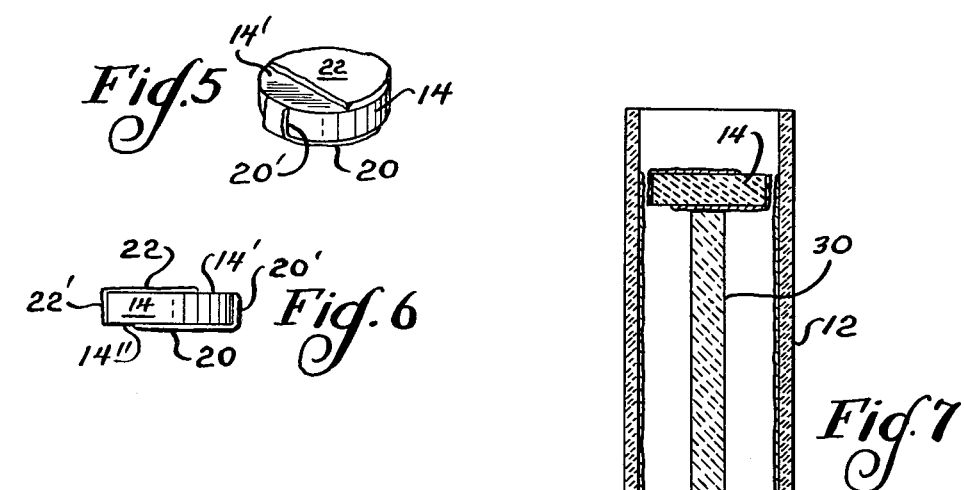
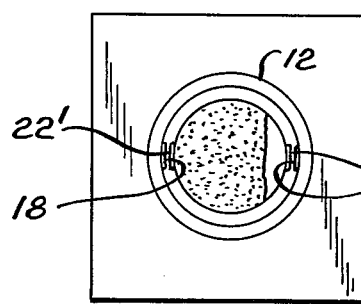
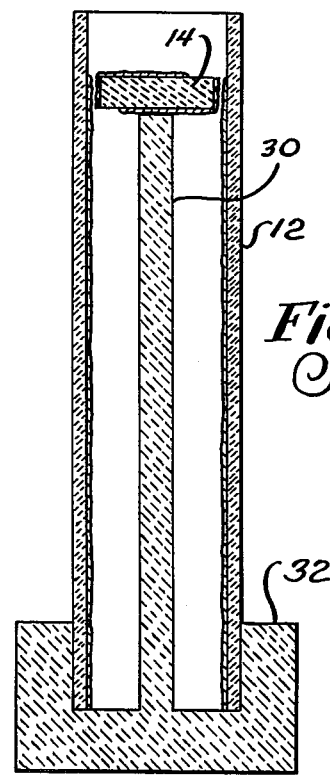

SOLID ELECTROLYTE OXYGEN SENSOR AND METHOD OF MAKING SAME

BACKGROUND OF THE INVENTION

The invention relates to oxygen sensors of the type incorporating a disc of stabilized solid electrolyte mounted in a ceramic tube of a non-electrolyte material. Two main problem areas which have arisen with such a construction relate to providing a hermetic seal which will hold the disc in the tube and attaching leads to the thin platinum electrodes on the faces of the disc. Although adequate solutions have been found individually for these problems, a substantial number of time consuming operations must be performed to produce a complete sensor assembly. For example, Shum et al U.S. Pat. No. 4,119,513 shows a sensor having an extremely uniform voltage response in which the platinum group metal leads to the platinum group metal electrodes extend the entire length of the tube, one inside and one outside, with the outside one extending over the sensing end of the tube to contact the sensing electrode. The disc is retained by a glass frit seal which has performed quite satisfactorily and is resistant to damage by thermal shock testing at temperatures of at least 1300° F. Davis U.S. Pat. No. 4,123,344 discloses a disc type electrolyte which is retained by the shrinkage of a ceramic tube during firing. The disc is supported in a recess and has internal and external leads which include junctures of different materials and certain additional assembly parts. Generally, the small shrinkages obtained with most ceramics requires very close control of the outer diameter of the disc and the diameter of the counterbore in which the disc is mounted. Also, where glass frit seals are used, there can be virtually no defects in the mating surfaces if a gas-tight seal is to be achieved.

SUMMARY

It is among the objects of the present invention to provide a disc type, tubular oxygen sensor which can be assembled quickly and economically and which has a wide tolerance range on the suitable dimensions of the disc and the ceramic tube in which it is mounted. Another object is to provide a means for attaching leads to the electrodes which is fast and simple, which protects the leads from damage, and which permits the leads to be formed of the same material as the electrodes so as to prevent secondary cells from being introduced which can produce erratic voltages.

These and other objects are achieved by the oxygen sensor and assembly method disclosed herein wherein a disc has continuous electrode coating applied to the major portion of each of its sensing and reference side surfaces and to a narrow band or stripe along one edge of the disc. The edge stripes are spaced from each other and, preferably, are diametrically opposed. A small portion of each of the sensing and reference side surfaces is left uncoated in the region immediately adjacent the edge band or stripe which is integrally connected to the opposite side surface. A coating of lead material, preferably the same as is applied to the disc as electrodes, is applied in a pair of stripes to the inner surface of the tube. The disc is placed on a pedestal and the tube, in a green state, is placed over it so that, during firing, the tube will shrink into an interference fit with the disc. The disc is pre-sintered and preferably made of yttria stabilized zirconia while the tube is preferably formed of fursterite which undergoes about a 25% shrinkage when it is fired to a temperature of about 2370° F. Satisfactory results have been achieved in a situation where the internal diameter of the green ceramic tube was about 20% larger than the outer diameter of the disc (0.460" and 0.383", respectively). The electrodes and leads are preferably formed of a platinum paste having a melting point for its glass frit binder of about 100°-200° F. below the firing temperature for the tube. During firing, the tube shrinks so as to cause about a 5% interference fit with the disc, producing a slight bulge in the area of the disc. The tube also glazes and tends to become mechanically sealed to the disc, both by the glaze and the pressure of the fit.

BRIEF DESCRIPTION OF THE DRAWINGS

FIG. 1 is a side cross-section showing the disc, tube and leads after firing;

FIG. 2 is a sectional view taken on line 2—2 of FIG. 1;

FIG. 3 is a side cross-section showing the tube before firing;

FIG. 4 is a top view of the tube of FIG. 3;

FIG. 5 is a perspective view of the disc with the electrodes coated thereon;

FIG. 6 is a side view of the disc of FIG. 5;

FIG. 7 is a side sectional view showing the jig in which the tube and disc are mounted for firing; and FIG. 8 is a top view of the structure shown in FIG. 7.

DETAILED DESCRIPTION OF THE INVENTION

Referring to FIG. 1, my improved oxygen sensor assembly indicated generally at 10 can be seen as consisting basically of a ceramic tubular body member 12 having a ceramic solid electrolyte disc 14 mounted therein near the upper or gas sensing end 12' thereof. The body is shown as being bulged outwardly slightly at 12" to illustrate the fact that the tube portions immediately axially adjacent to the disc are shrunk into an interference relationship with the disc 14 during a firing operation. Although not shown, the sensor assembly 10 is, during use, generally mounted in a housing that allows its sensing end 12' to be immersed in the gases to be sensed, typically flue gases, while the outer or reference end 12" is in communication with ambient air. In such a mounting the sensing side 14' and the reference side 14" of the electrolyte are exposed to gases having different partial pressures of oxygen. As is well known, the difference in oxygen partial pressures generates a voltage in the solid electrolyte cell 14 which can be measured by circuitry (not shown) attached to the terminal ends 16' and 18' of the reference electrode lead member 16 and the sensing electrode lead member 18, respectively. These lead members 16, 18 are preferably made of platinum and are in firm bonding contact with the reference electrode 20 and the sensing electrode 22 which are also preferably made of platinum so there will be no dissimilar metals in the sensor which could generate unwanted voltages.

The sensor assembly 10 is assembled by first taking the initial process step illustrated in FIG. 7. In this step, one takes a sintered solid electrolyte disc or wafer 14 which has had electrode paste coatings 20, 20' and 22, 22' applied to it as shown in FIGS. 5 and 6 and places it on a pedestal 30 carried by a ceramic firing fixture 32 so that it will be held in a predetermined axial position relative to the unfired or green ceramic tube 12 shown in FIGS. 3 and 4. The disc 14 is positioned so that the electrode stripe portions 20', 22' will be aligned with the lead stripe portions 16, 18, respectively, on the tube 12, as shown in FIG. 8. The fixture 32 can then be placed in an oven for firing the tube 12 and causing it to shrink into firm mechanical contact with the disc 14 as illustrated in FIG. 1. Where the tube material is forsterite having a shrinkage during firing of about 25%, the outer diameter of the disc 14 and the inner diameter of the tube 12 can vary in dimension by 20% and still provide a 5% interference fit. This is an important advantage in assembly since it means that the tolerances on the discs and on the extruded green ceramic tubes can be quite loose. Also, no recess must be machined into the tube for the disc to be seated in. Furthermore, by avoiding the change in tube wall cross-section which a recess provides the capability of the sensor to resist thermal shock is enhanced.

I claim as my invention:

1. A method of making an oxygen sensing device comprising the steps of:

forming a sintered wafer of stabilized solid electrolyte ceramic;

applying a first, porous, continuous electrode coating to the major portion of the sensing side of said wafer and to a narrow first band portion along the axial length of a first side edge portion of said wafer while leaving said sensing side of said wafer devoid of said electrode coating in the area thereof which is immediately adjacent a second side edge portion which is circumferentially spaced from said first band of coating;

applying a second, porous, continuous electrode coating to the major portion of the reference side of said wafer and to a narrow second band portion along the axial length of said second side edge portion while leaving said reference side of said wafer devoid of said electrode coating in the area thereof which is immediately adjacent said first narrow band portion;

applying first and second spaced conductive stripes internally along at least a portion of the length of an unfired ceramic tube having an inner diameter greater than the outer diameter of said wafer and a temperature coefficient of expansion which is compatible with said wafer after firing but will cause said tube to shrink into a hermetic sealing relationship with said wafer during firing, said stripes being applied at a circumferential spacing corresponding to the spacing between said first and second bands of coating;

positioning said wafer internally of said unfired ceramic tube so that its first and second bands of coating are aligned with and overlie said first and second conductive stripes; and firing said tube and wafer assembly to shrink said tube onto said wafer and mechanically force said bands of coating into intimate contact with said conductive stripes.

2. A method in accordance with claim 1 wherein said ceramic tube is formed by extrusion.

3. A method in accordance with claim 1 wherein said tube is formed of a material which will shrink about 25% when it is fired.

4. A method in accordance with claim 3 wherein said electrode coatings on said wafer and said conductive stripes on said tube are of the same material, said stripes extending internally of said tube to the reference end thereof.

5. A method in accordance with claim 4 wherein said tube is formed so that its walls have a substantially constant thickness cross-section throughout their length.

6. An oxygen sensing device comprising a ceramic tube having a relatively uniform wall thickness; a thin wafer of stabilized solid electrolyte material positioned intermediate the ends of said tube and transverse to the axis thereof, said wafer having a sensing side and a reference side, the outer diameter of said wafer being greater than the inner diameter of said tube in at least the spaced axial regions of said tube which are immediately adjacent the two sides of said wafer, and the outer diameter of said ceramic tube being greater in the plane of said wafer than in the transverse axial planes immediately adjacent thereto, said difference in diameters being sufficient to hermetically seal said wafer into said ceramic tube throughout a temperature range of at least about 500°–2000° F.; a first, continuous, porous electrode coating on the major portion of the sensing side of said wafer and along a first narrow band on the side edge of said wafer; a second, continuous porous electrode coating on the major portion of the reference side of said wafer and along a second, narrow band on the side edge of said wafer which is spaced circumferentially around said wafer from said first coating band, said sensing and reference sides being devoid of coating in the regions thereof which are immediately adjacent said second and first coating bands, respectively; first and second, axially extending, spaced conductive stripes positioned along the interior of said ceramic tube from the reference end thereof to at least the sensing edge of said wafer, said first and second conductive stripes being aligned with, and in intimate electrical and mechanical contact with said first and second coating bands, respectively.

7. The oxygen sensing device of claim 6 wherein said electrode coatings and said conductive stripes are of the same material.

8. The oxygen sensing device of claim 7 wherein said tube is formed of forsterite.

* * * * *